US008693704B2

(12) United States Patent
Kim et al.

(10) Patent No.: US 8,693,704 B2
(45) Date of Patent: Apr. 8, 2014

(54) METHOD AND APPARATUS FOR CANCELING NOISE FROM MIXED SOUND

(75) Inventors: Kyu-hong Kim, Yongin-si (KR); Kwang-cheol Oh, Yongin-si (KR); Jae-hoon Jeong, Yongin-si (KR); So-young Jeong, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1672 days.

(21) Appl. No.: 12/078,551

(22) Filed: Apr. 1, 2008

(65) Prior Publication Data

US 2009/0129610 A1 May 21, 2009

(30) Foreign Application Priority Data

Nov. 15, 2007 (KR) ........................ 10-2007-0116763

(51) Int. Cl.
*H04B 15/00* (2006.01)
*G10K 11/16* (2006.01)
*A61F 11/06* (2006.01)

(52) U.S. Cl.
USPC ......................................... 381/94.7; 381/71.1

(58) Field of Classification Search
None
See application file for complete search history.

(56) References Cited

U.S. PATENT DOCUMENTS 5,732,143 A * 3/1998 Andrea et al. ............... 381/71.6
7,577,262 B2 * 8/2009 Kanamori et al. ........... 381/94.7
2008/0152167 A1 * 6/2008 Taenzer ....................... 381/94.2
2008/0175408 A1 * 7/2008 Mukund et al. .............. 381/94.1

FOREIGN PATENT DOCUMENTS

KR 10-2005-0000006 1/2005
KR 10-2007-0007697 A1 1/2007

OTHER PUBLICATIONS

Notice of Non-Final Rejection for Korean Application No. 10-2007-0116763 dated Dec. 20, 2013.

* cited by examiner

*Primary Examiner* — Hrayr A Sayadian
(74) *Attorney, Agent, or Firm* — Staas & Halsey LLP

(57) ABSTRACT

A method, medium, and apparatus canceling noise from a mixed sound. The method includes receiving sound source signals including a target sound and noise, extracting at least one feature vector indicating an attribute difference between the sound source signals from the sound source signals, calculating a suppression coefficient considering ratios of noise to the sound source signals based on the at least one extracted feature vector, and canceling the sound source signals corresponding to noise by controlling an intensity of an output signal generated from the sound source signals according to the calculated suppression coefficient. Accordingly, a clear target sound source signal can be obtained.

19 Claims, 7 Drawing Sheets

METHOD AND APPARATUS FOR CANCELING NOISE FROM MIXED SOUND

CROSS-REFERENCE TO RELATED APPLICATIONS

This application claims the benefit of Korean Patent Application No. 10-2007-0116763, filed on Nov. 15, 2007, in the Korean Intellectual Property Office, the disclosure of which is incorporated herein in its entirety by reference.

BACKGROUND

1. Field

One or more embodiments of the present invention relates to a method, medium and apparatus for canceling noise from a mixed sound, and more particularly, to a method, medium, and apparatus for canceling sound source signals corresponding to interference noise, thereby maintaining a target sound source signal, from a mixed sound input from a digital recording device having a microphone array for acquiring a mixed sound from a plurality of sound sources.

2. Description of the Related Art

Calling, recording an external sound, or acquiring a moving picture by using a portable digital device has become widely popular. A microphone is used to acquire a sound in various digital devices, such as consumer electronics (CE) devices and portable phones, wherein a microphone array instead of just one microphone is generally used to implement a stereo sound using two or more channels instead of a mono sound of a single channel.

Meanwhile, an environment in which a sound source is recorded or a sound signal is input by way of a portable digital device will commonly include various kinds of noise and ambient interference sounds, rather than being a calm environment without ambient interference sounds. Thus, technologies for strengthening only a specific sound source signal required by a user or canceling unnecessary ambient interference sounds from a mixed sound are being developed.

SUMMARY

One or more embodiments of the present invention provides a noise canceling method, medium and apparatus for acquiring a target sound, such as a voice of a user, from a mixed sound in which the target sound is mixed with interference noise radiated from various sound sources around the user.

Additional aspects and/or advantages will be set forth in part in the description which follows and, in part, will be apparent from the description, or may be learned by practice of the invention.

According to an aspect of the present invention, there is provided a noise canceling method including locating at the same distance from a target sound source and receiving sound source signals including a target sound and noise, extracting at least one feature vector indicating an attribute difference between the sound source signals from the sound source signals, calculating a suppression coefficient considering ratios of noise to the sound source signals based on the at least one extracted feature vector, and canceling at least one sound source signal, of the sound source signals, corresponding to noise by controlling an intensity of an output signal generated from the sound source signals according to the calculated suppression coefficient.

According to another aspect of the present invention, there is provided a computer readable medium including computer readable code to control at least one processing element to implement such a noise canceling method.

According to another aspect of the present invention, there is provided a noise canceling apparatus including a plurality of acoustic sensors locating at the same distance from a target sound source and receiving sound source signals including a target sound and noise, a feature vector extractor extracting at least one feature vector indicating an attribute difference between the sound source signals from the sound source signals, a suppression coefficient calculator calculating a suppression coefficient considering ratios of noise to the sound source signals based on the at least one extracted feature vector, and a noise signal canceller canceling at least one sound source signal, of the sound source signals, corresponding to noise by controlling an intensity of an output signal generated from the sound source signals according to the calculated suppression coefficient.

BRIEF DESCRIPTION OF THE DRAWINGS

These and/or other aspects and advantages will become apparent and more readily appreciated from the following description of the embodiments, taken in conjunction with the accompanying drawings of which.

DETAILED DESCRIPTION OF EMBODIMENTS

Figure 1A:
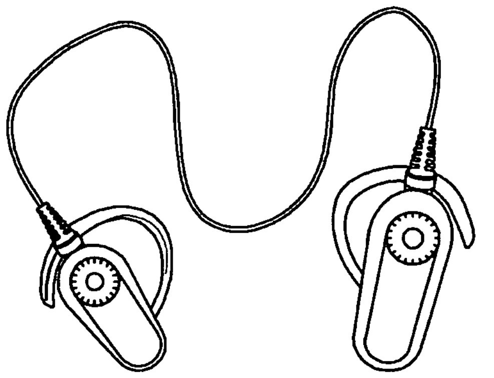
FIGS. 1A and 1B illustrate acoustic sensors, according to an embodiment of the present invention.

Reference will now be made in detail to embodiments, examples of which are illustrated in the accompanying drawings, wherein like reference numerals refer to like elements throughout. In this regard, embodiments of the present invention may be embodied in many different forms and should not be construed as being limited to embodiments set forth herein. Accordingly, embodiments are merely described below, by referring to the figures, to explain aspects of the present invention.

In the embodiments described below, a sound source means a source from which sound is radiated, and a sound pressure means a force derived from acoustic energy, which is represented using a physical amount of pressure.

Figure 1B:
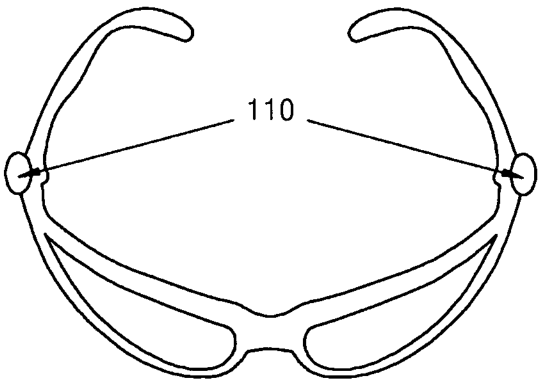

FIGS. 1A and 1B illustrate acoustic sensors, according to an embodiment of the present invention, respectively illustrating a headset equipped with microphones and glasses equipped with microphones.

According to the miniaturization of various electronic parts, digital convergence products having two or more operations, such as phone calling, music playing, video reproducing, and game playing, in one digital device have become widely available. For example, portable phones have been developed as digital hybrid devices by adding an MP3 player operation for listening to music or a digital camcorder operation for capturing video.

A hands-free headset is commonly used as a tool for allowing a user to make a call using such a portable phone without using his or her hands. This hands-free headset generally transmits and receives a mono-channel sound signal to one ear of a user. Meanwhile, a hands-free headset available for portable phones having the MP3 player operation are used not only to transmit and receive a single-channel sound signal for simple calling but also to listen to music or listen to sound while playing video. Thus, when a user desires to listen to music or listen to sound while playing video, a hands-free headset must support a stereo channel instead of a mono channel and have a figure of a full headset for listening to music by attaching it to both ears of the user instead of one ear.

In the point of view described above, FIG. 1A illustrates a headset that may be attached to both ears of a user, and it can be assumed that this hands-free headset has speakers for listening to sound and microphones for acquiring sound from the outside. It is assumed that a total of two microphones are respectively equipped in left and right units of the hands-free headset. Hereinafter, the microphones for acquiring sound will be mainly described as those from among the speakers and the microphones equipped in the hands-free headset.

In general, since a distance between the mouth of the user and any one of the microphones is far in the miniaturized hands-free headset illustrated in FIG. 1A, it is difficult to clearly acquire sound spoken by the user by using only a single microphone. Thus, in the embodiments of the present invention, a voice of a user is more clearly acquired by using microphones equipped in both units of a hands-free headset.

It is known that sound is propagated at a speed of 340 Km/sec in the air. Thus, a longer time is needed for a sound wave to reach a place farther from a sound source. In addition, even if sound waves are propagated along different paths from the sound source, if the moving distances are the same, arrival times are also the same. That is, arrival times of the sound waves to two places that are apart by the same distance from the sound source are the same, and arrival times of the sound waves to two places that are apart by different distances from the sound source are different. Based on the above, FIG. 2 will now be described.

Figure 2:
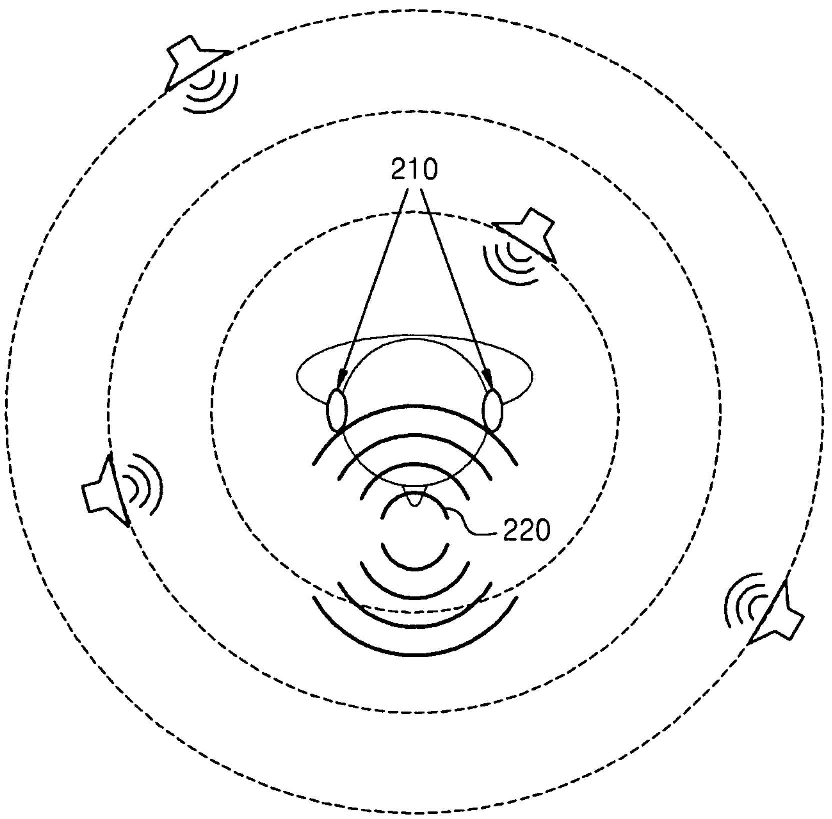
FIG. 2 illustrates a problem occurrence status to be solved by the embodiments and an environment in which an acoustic sensor is used, according to the embodiments of the present invention.

FIG. 2 illustrates a problem occurrence status to be solved by embodiments and an environment in which an acoustic sensor is used, according to embodiments of the present invention. In the center of FIG. 2, a user is located, and concentric circles visually show locations having the same distance from the user for convenience of description. It is assumed that the user has a hands-free headset 210 as illustrated in FIG. 1A, which is attached to both ears of the user. In addition, it is assumed that interference noise is generated by four individual sound sources located around the user and the user is speaking during a phone call. Since the voice spoken from the mouth of the user is also a sound source, a waveform 220 through which sound is propagated is visually shown.

In this situation, the interference noise propagated from the four sound sources and the voice propagated from the mouth of the user may be input to microphones equipped in the hands-free headset 210 attached to the user. A caller will want to hear only the voice of the user without the interference noise around the user. Thus, in various embodiments of the present invention to be described hereinafter, interference noise is cancelled from a mixed sound input through a plurality of microphones in order to reserve only a target sound source signal. Under this problematic situation, according to the sound propagation principle described in relation to FIG. 1A, features in an environment in which the embodiments of the present invention are used are as follows.

First, the two microphones equipped in the hands-free headset 210 attached to the user have the same distance from a target sound source (indicating the mouth of the user). Thus, arrival times of sound waves from the target sound source are the same. Second, the four sound sources located around the user have different distances to the two microphones equipped in the hands-free headset 210 attached to the user. Thus, interference noise propagated from each of the four sound sources reaches the two microphones at different times. Based on the features described above, the hands-free headset 210 attached to the user can distinguish the voice spoken by the user from interference noise by using the difference between arrival times of sound waves to the two microphones. That is, a target sound has no arrival time difference between sound waves, and interference noise has an arrival time difference between sound waves.

These features are based on the fact that two microphones are located at the same distance from a target sound source. FIG. 1B illustrates a configuration that two microphones 110 are attached to glasses or sunglasses as an embodiment of the present invention. Thus, it will be understood by one of ordinary skill in the art that the embodiment can be applied not only to the hands-free headset and the glasses illustrated in FIGS. 1A and 1B, but also to various acoustic sensors located the same distance from a target sound source.

In particular, in the situations illustrated in FIGS. 1A, 1B, and 2, due to the fact that the head of a user is located between two microphones, it is easier to distinguish a target sound from interference noise because a difference between arrival times for sound waves propagated from a single sound source to reach the microphones is greater as a microphone array acquiring a mixed sound are farther from each other. That is, since the head of a user is located between two microphones, a difference between amplitudes of receive channels (indicating the two microphones) is much greater for propagated interference noise from the point of view of the user.

Due to these features, symmetric signals having the same distance between a sound source and microphones can be considered as a target sound, and asymmetric signals having different distances between a sound source and the microphones can be considered as interference noise. Thus, a method is suggested, of cancelling noise from a mixed sound by relatively maintaining or strengthening the sound source signal considered as the target sound and relatively suppressing the sound source signals considered as the interference noise. Hereinafter, various embodiments for cancelling noise signals from a mixed sound to reserve a target sound source signal will be described based on the features described above by indicating a difference between a target sound and interference noise.

Figure 3:
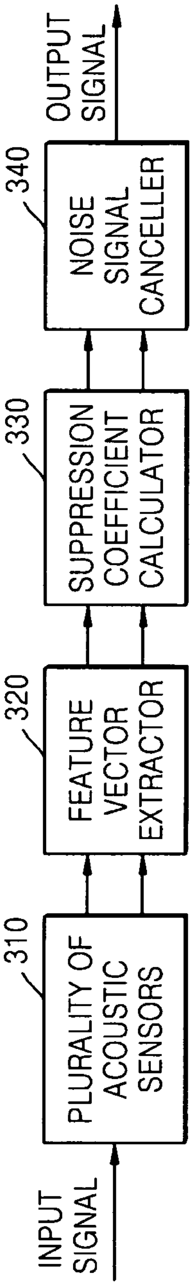
FIG. 3 is a block diagram of a noise canceling apparatus, according to an embodiment of the present invention.

FIG. 3 is a block diagram of a noise canceling apparatus, according to an embodiment of the present invention. Herein, the term apparatus should be considered synonymous with the term system, and not limited to a single enclosure or all described elements embodied in single respective enclosures in all embodiments, but rather, depending on embodiment, is open to being embodied together or separately in differing enclosures and/or locations through differing elements, e.g., a respective apparatus/system could be a single processing element or implemented through a distributed network, noting that additional and alternative embodiments are equally available.

Referring to FIG. 3 the noise canceling apparatus, according to an embodiment of the present invention, includes a plurality of acoustic sensors 310, a feature vector extractor 320, a suppression coefficient calculator 330, and a noise signal canceller 340.

The plurality of acoustic sensors 310 receive a mixed sound containing a target sound and interference noise from the outside. The acoustic sensor 310 is a device for acquiring sound propagated from a sound source, for example, a microphone.

The feature vector extractor 320 extracts at least one feature vector indicating an attribute difference between sound source signals from the sound source signals corresponding to the received mixed sound. The attribute of a sound source signal indicates a sound wave characteristic, such as amplitude or phase, of the sound source signal. The attribute may be different according to a time taken for sound propagated from a sound source to reach an acoustic sensor, a reaching distance, or a characteristic of the initially radiated sound. The feature vector is a kind of index or standard indicating an attribute difference between sound source signals, as described based on the attribute of a sound source signal, and the feature vector may be an amplitude ratio or phase difference between sound source signals.

A process of extracting a feature vector in the feature vector extractor 320 will now be described in more detail.

It is assumed for convenience of description that the acoustic sensors 310 are the left and right microphones in the hands-free headset described in FIG. 1A. Two mixed signals input through the microphones are divided into individual frames. The frame indicates a unit obtained by dividing a sound source signal into predetermined sections according to a time change, and in general, in order to finitely limit a signal input to a system for digital signal processing, the signal is processed by being divided into predetermined sections called frames. This frame dividing process is implemented by using a specific filter called a window operation used to divide a single sound source signal that is continuous according to time into frames. A representative example of the window operation is a Hamming window that will be easily understood by one of ordinary skill in the art.

The sound source signals divided into frames are transformed from the time domain to the frequency domain by using fast Fourier transformation (FFT) for convenience of computation. Frequency components in each frame extracted for the input two mixed signals are represented by the below Equation 1, for example.

$$X_R(w_k,n)$$

$$X_L(w_k,n) \qquad \text{Equation 1}$$

Here, n denotes a frame index in the time domain, k denotes an index of a frequency bin which is a unit section when a sound source signal is time-frequency transformed, and $w_k$ denotes a $k^{th}$ frequency value. That is, Equation 1 indicates a $k^{th}$ frequency component (physically denotes an energy amount of an input signal) in an $n^{th}$ frame of each of right and left channels and is defined with a complex value.

An amplitude and phase change between channels (indicating the two microphones) can be represented with a feature vector by way of calculation for every frequency component, and in the current embodiment, shown in the below Equations 2 and 3, for example.

$$f_1(w_k, n) = \max\left(\frac{|X_R(w_k, n)|}{|X_L(w_k, n)|}, \frac{|X_L(w_k, n)|}{|X_R(w_k, n)|}\right) \qquad \text{Equation 2}$$

Equation 2 is an equation for calculating a ratio of absolute values of frequency components indicating energy amounts of the right and left channels, and $f_1(w_k, n)$ denotes an amplitude ratio between sound source signals for a mixed sound input through the two microphones. If a target sound source signal is dominant among the input mixed sound, frequency components of the two mixed signals are almost the same, and thus the amplitude ratio $f_1(w_k, n)$ of Equation 2 will be relatively close to 1 as compared to a case in which a noise signal is dominant.

Equation 2 is designed to calculate the maximum value of two amplitude ratios since it is necessary that the calculation result is limited to have a specific range for convenience of comparison with a threshold value to be described later, and one of ordinary skill in the art will be able to design various equations for calculating an amplitude ratio by using representations different from the suggestion of Equation 2. In addition, the value of $f_1(w_k, n)$ will be able to be calculated as a log power spectrum difference by being transformed to a log scale besides the amplitude ratio.

$$f_2(w_k,n) = \angle X_R(w_k,n) - \angle X_L(w_k,n) \qquad \text{Equation 3}$$

Here, $\angle$ denotes an angle shown when each of frequency components $X_R$ and $X_L$ of the right and left channels defined with a complex value are drawn on a complex plane, i.e., denotes a phase of both signals. Thus, Equation 3 indicates a phase difference between the sound source signals for the mixed sound input to the two microphones. If a target sound source signal is dominant among the input mixed sound, frequency components of the two mixed signals are almost the same, and thus the phase difference $f_2(w_k, n)$ of Equation 3 will be relatively close to 0 as compared to a case in which a noise signal is dominant.

As described above, an amplitude ratio and a phase difference between sound source signals illustrated as a feature vector by using Equations 2 and 3 were described. A method of canceling noise by using a calculated feature vector will now be described.

The suppression coefficient calculator 330 calculates a suppression coefficient considering ratios of noise to the sound source signals based on the feature vector extracted by the feature vector extractor 320. The suppression coefficient indicates a parameter for determining how much a sound source signal is suppressed. In a sound source signal in a specific frequency component, a signal corresponding to noise may be dominant, or a signal corresponding to voice (indicating a target sound) may be dominant. In the current embodiment of the present invention, a method of canceling interference noise by suppressing a frequency component in which a signal corresponding to noise is dominant is suggested. To do this, the suppression coefficient calculator 330 calculates a suppression coefficient for each frequency component. If a sound source signal is close to a target sound desired by a user, the sound source signal will be scarcely suppressed, and if the sound source signal is close to interference noise not desired by the user, the sound source signal will be almost suppressed. Whether the sound source signal is close to a target sound or interference noise will be determined by comparing a noise ratio of the sound source signal to a specific reference value. A process of calculating a suppression coefficient considering a noise ratio of a sound source signal in the suppression coefficient calculator 330 will now be described in more detail with reference to FIG. 4.

Figure 4:
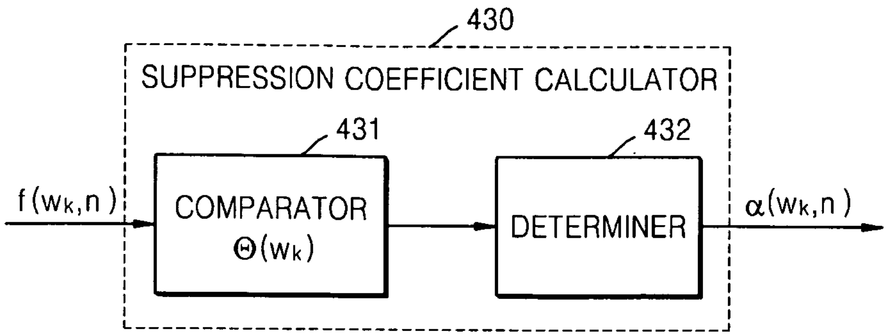
FIG. 4 is a block diagram of a suppression coefficient calculator included in a noise canceling apparatus, according to an embodiment of the present invention.

FIG. 4 is a block diagram of a suppression coefficient calculator 430 included in a noise canceling apparatus, according to an embodiment of the present invention. Referring to FIG. 4, the suppression coefficient calculator 430, according to an embodiment of the present invention, includes a comparator 431 and a determiner 432.

The comparator 431 compares a feature vector extracted by a feature vector extractor (not shown) and a specific threshold value. The specific threshold value is a reference value preset to determine whether a sound source signal is close to a target sound source signal or a noise signal by considering a ratio of the target sound source signal and the noise signal included in the sound source signal.

The determiner 432 determines a relative dominant state between the target sound source signal and the noise signal included in the sound source signal based on the comparison result performed by the comparator 431. As described above, the relative dominant state between the target sound source signal and the noise signal included in the sound source signal is obtained by comparing the feature vector and the specific threshold value, and the specific threshold value can be differently set according to the type feature vector and appropriately controlled according to the requirements of an environment in which the current embodiment of the present invention is used.

For example, in a case in which a feature vector is an amplitude ratio between sound source signals, when it is determined in a sound source signal whether a characteristic of a target sound source signal or a noise signal is dominant, an existing ratio of each of the both signals is not necessarily 50%. In an environment that is acceptable even though an existing ratio of a noise signal is 60%, the threshold value described above can be set to correspond to 60%.

A method of comparing the feature vector and the threshold value can be achieved by comparing an absolute value of the feature vector and the threshold value and may be designed by using more complicated environmental variables. Equation 4, below, is an example comparison equation designed considering complicated environmental variables.

$$\alpha(w_k, n) = \begin{cases} \gamma \cdot 1 + (1-\gamma)\cdot\alpha(w_k, n-1), & \text{if } |f_1(w_k, n)| < \Theta_1(w_k) \text{ and } |f_2(w_k, n)| < \Theta_2(w_k) \\ \gamma \cdot c_1 + (1-\gamma)\cdot\alpha(w_k, n-1), & \text{if } |f_1(w_k, n)| < \Theta_1(w_k) \text{ and } |f_2(w_k, n)| \geq \Theta_2(w_k) \\ \gamma \cdot c_2 + (1-\gamma)\cdot\alpha(w_k, n-1), & \text{if } |f_1(w_k, n)| \geq \Theta_1(w_k) \text{ and } |f_2(w_k, n)| < \Theta_2(w_k) \\ \gamma \cdot c_3 + (1-\gamma)\cdot\alpha(w_k, n-1), & \text{otherwises} \end{cases} \quad \text{Equation 4}$$

Here, $\alpha(w_k, n)$ denotes a suppression weight (indicating a noise suppression coefficient) of a $k^{th}$ frequency component in an $n^{th}$ frame, and is close to 1 if a difference between sound source signals input through the two channels is physically small, and is close to 0 if the difference is large. Since the noise suppression coefficient has a value less than 1, in a noise dominant signal, an effect is manifested whereby a noise component included in a sound source signal relatively decreases as compared to a voice component (indicating a target sound). In addition, since $\alpha(w_k, n)$ denotes a noise suppression coefficient in the $n^{th}$ frame, $\alpha(w_k, n-1)$ denotes a noise suppression coefficient in a previous frame of $\alpha(w_k, n)$.

$\theta_1(w_k)$ and $\theta_2(w_k)$ are respective threshold values of the feature vectors $f_1(w_k, n)$ and $f_2(w_k, n)$. $c_k$ is a noise suppression constant that satisfies $0 \leq c_3 < c_2 < c_1 < 1$, and increases as noise contained in a sound source signal becomes more dominant. In addition, $\gamma$ is a learning coefficient that is a constant satisfying $0 \leq \gamma \leq 1$, and denotes a ratio for reflecting a past value to a currently estimated value. As the learning coefficient increases, the past value is less reflected. For example, if the learning coefficient is 1, the past value, i.e., the noise suppression coefficient $\alpha(w_k, n-1)$ in a previous step, is eliminated.

Equation 4 illustrates four cases in which the feature vector regarding an amplitude ratio $f_1(w_k, n)$ and the feature vector regarding a phase difference $f_2(w_k, n)$ are respectively compared to threshold values $\theta_1(w_k)$ and $\theta_2(w_k)$. The top case is a case where the two feature vectors are less than the respective threshold values, indicating that an amplitude difference or a phase difference between sound source signals barely exists. That is, it means that the sound source signal is a signal close to a target sound source signal. On the contrary, the latter case means that the sound source signal is a signal close to a noise signal.

Equation 4 is an embodiment illustrating a design of a noise suppression coefficient considering various environmental variables, wherein two feature vectors are used, and one of ordinary skill in the art may suggest a method of designing a suppression coefficient calculation method using three or more feature vectors.

A process of calculating a suppression coefficient in the suppression coefficient calculator 430 has been described. A process of canceling a noise signal by using the calculated suppression coefficient will now be described by referring back to FIG. 3.

The noise signal canceller 340 cancels a noise signal contained in the sound source signals by controlling the intensity of an output signal induced from the sound source signals according to the suppression coefficient calculated by the suppression coefficient calculator 330.

As described above, since the acoustic sensors 310 are plural, the number of sound source signals input through the acoustic sensors 310 corresponds to the number of acoustic sensors 310. Thus, a process of generating a single output signal from the plurality of sound source signals is necessary. The process of generating a single output signal can be achieved according to a pre-set specific operation (hereinafter, an output signal generation operation) and is basically a signal induced from the sound source signals. Simply, an output signal can be determined by averaging the plurality of sound source signals or selecting one signal from among the plurality of sound source signals. In addition, the output signal generation operation can be properly updated or modified according to environments in which various embodiments of the present invention are implemented.

A method of controlling the intensity of an output signal according to a suppression coefficient in the noise signal canceller 340 will now be described in more detail with reference to FIG. 5.

Figure 5:
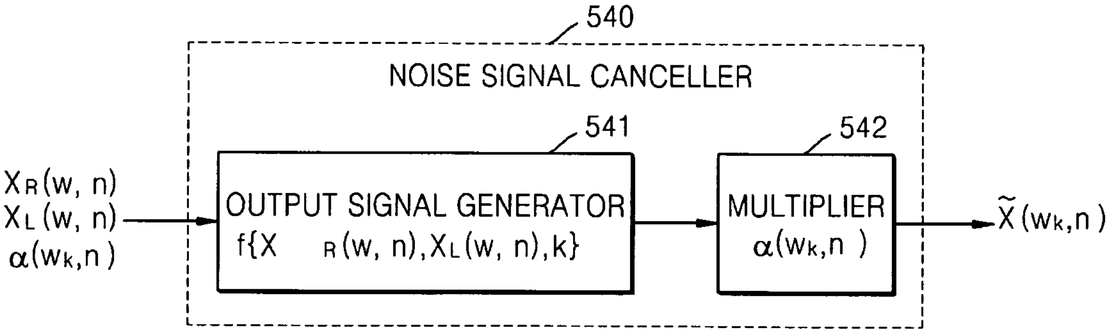
FIG. 5 is a block diagram of a noise signal canceller included in a noise canceling apparatus, according to an embodiment of the present invention.

FIG. 5 is a block diagram of a noise signal canceller 540 included in a noise canceling apparatus, according to an embodiment of the present invention. Referring to FIG. 5, the noise signal canceller 540, according to an embodiment of the present invention, includes an output signal generator 541 and a multiplier 542.

The output signal generator 541 generates an output signal according to a specific rule by receiving sound source signals input through acoustic sensors (not shown). The specific rule refers to the output signal generation operation described above. In the current embodiment, since it is assumed that two microphones are used as the acoustic sensors, the input sound source signals are sound source signals of two right and left channels. Thus, the output signal generator 541 inputs the sound source signals of the two channels to the output signal generation operation and obtains a single output signal as a result.

The multiplier 542 cancels noise from the output signal generated by the output signal generator 541 by multiplying the output signal by a suppression coefficient calculated by a suppression coefficient calculator (not shown). As described above, since the suppression coefficient is calculated considering an existing ratio of noise contained in the sound source signal, an effect of canceling a noise signal occurs by multiplying the sound source signal by the calculated suppression coefficient.

When the above process is represented using a generalized output signal generation operation, the below Equation 5 may be defined.

$$\tilde{X}(w_k,n)=f\{X_R(w,n),X_L(w,n),k\}\times\alpha(w_k,n) \quad \text{Equation 5}$$

Here, $\tilde{X}(w_k,n)$ denotes a final output signal from which noise is cancelled, $f\{X_R(w,n),X_L(w,n),k\}$ denotes an operation of generating an output signal by receiving right and left sound source signals of a $k^{th}$ frequency component as parameters, and $\alpha(w_k, n)$ denotes a suppression coefficient.

As described above, the output signal generation operation is based on input sound source signals. As a user speaks, if sound source signals input to a plurality of acoustic sensors are the same, one of the sound source signals can be selected. However, when interference noise is present, if input sound source signals are different from each other, an output signal can be obtained by calculating a mean value of the sound source signals as represented by the below Equation 6, for example.

$$\tilde{X}(w_k,n)=0.5*\{X_R(w_k,n)+X_L(w_k,n\}\times\alpha(w_k,n) \quad \text{Equation 6}$$

This mean value can be obtained by a delay-and-sum beam-former using a sum of signals between channels.

In general, a microphone array formed with two or more microphones acts as a filter for spatially reducing noise in a case where a desired target signal and an interference noise signal have different directions, by enhancing an amplitude by properly weighting each signal received by the microphone array in order to receive a target signal mixed with background noise. This kind of spatial filter is called a beam-former. Various methods using the beam-former are well known, and a beam-former having a structure for adding a delayed sound source signal reaching each microphone is called a delay-and-sum algorithm. That is, an output value of a beam-former receiving and adding sound source signals having a difference between arrival times to channels is an output signal obtained by way of the output signal generation operation.

Besides the method using a mean value, another output signal generation operation may be represented by the below Equation 7.

$$\tilde{X}(w_k,n)=\min\{X_R(w_k,n),X_L(w_k,n)\}\times\alpha(w_k,n) \quad \text{Equation 7}$$

Equation 7 suggests a method of selecting a signal having a lesser energy value from among right and left input signals as an output signal. In general, a user's voice is equally input to two channels, whereas interference noise is more input to a channel closer to an interference sound source. Thus, in order to suppress a noise signal, it will be effective to select a sound source signal having a lesser energy value from among the two input signals. That is, Equation 7 illustrates a method of selecting a signal having a lesser noise influence as an output signal.

A major configuration of a noise canceling apparatus according to an embodiment of the present invention has been described. The noise canceling apparatus according to an embodiment of the present invention shows an effect of effectively canceling out interference noise without having to calculate a direction of a target sound source, due to the distance from the target sound source to acoustic sensors being the same. In addition, since future data is unnecessary for digital signal processing of a current frame of a sound source signal, noise cancellation is performed in real-time, and as a result, quick signal processing without any delay can be performed.

Two additional embodiments based on the above-described embodiments will now be described.

Figure 6:
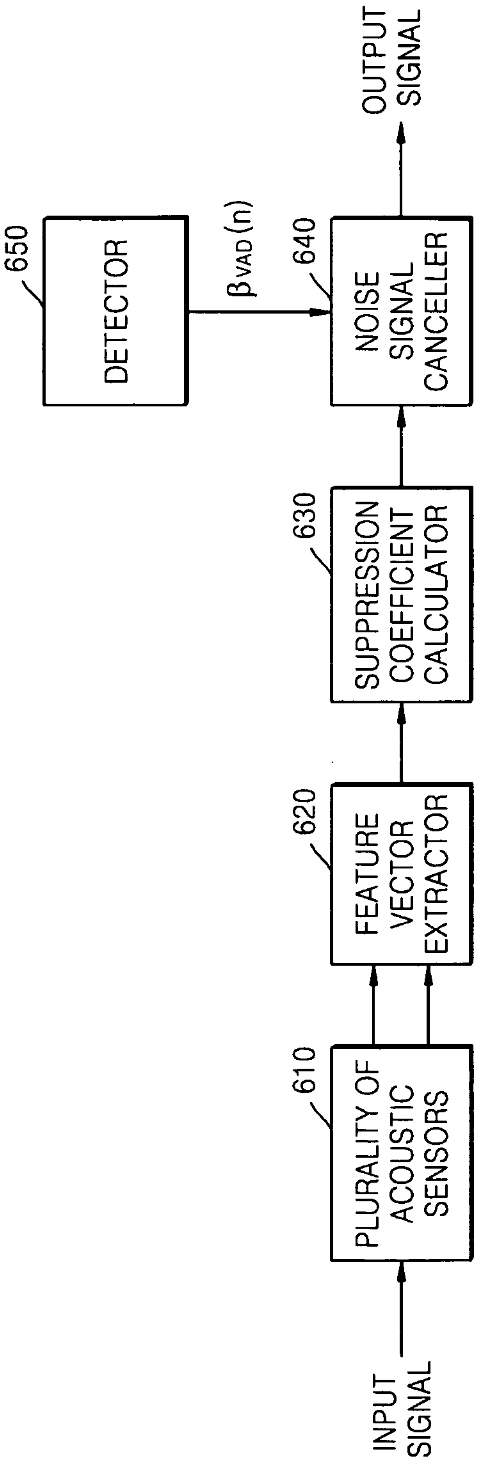
FIG. 6 is a block diagram of a noise canceling apparatus, which includes a configuration for detecting whether a target sound source signal exists, according to another embodiment of the present invention.

FIG. 6 is a block diagram of a noise canceling apparatus, which includes a configuration for detecting whether a target sound source signal exists, according to another embodiment of the present invention. Referring to FIG. 6, a detector 650 is added to the block diagram illustrated in FIG. 3. Since a plurality of acoustic sensors 610, a feature vector extractor 620, a suppression coefficient calculator 630, and a noise signal canceller 640 were described with reference to the embodiment illustrated in FIG. 3, mainly only the detector 650 will now be described.

The detector 650 detects a section in which a target sound source signal does not exist from sound source signals using an arbitrary voice detection method. That is, when a section in which a user speaks and a section in which interference noise is generated are mixed in a series of sound source signals, the detector 650 correctly detects only the section in which the user speaks. In order to determine whether the target sound source signal exists in a current voice signal frame, a method, such as calculation of an energy value (or a sound pressure) of a frame, estimation of a signal-to-noise ratio (SNR), or voice activity detection (VAD), can be used, and hereinafter, the VAD method will be mainly described.

VAD is used to identify a voice section in which a user speaks and a silent section in which the user does not speak. By canceling a sound source signal corresponding to a silent section when the silent section is detected from a sound source signal by using VAD, an effect of canceling interference noise except for a user's voice can be increased.

Various methods are disclosed to implement the VAD, and among them, methods using a bone conduction microphone or a skin vibration sensor have been recently introduced. In particular, since the methods using a bone conduction microphone or a skin vibration sensor operate by being directly attached to a user's body, the methods have a characteristic of being robust to interference noise propagated from an external sound source. Thus, by using VAD in the noise canceling apparatus according to the current embodiment, a great performance increase in terms of noise cancellation can be achieved. Since a method of detecting a section in which a target sound source signal exists using VAD can be easily understood by one of ordinary skill in the art, the method will not be described.

The noise signal canceller 640 cancels a sound source signal corresponding to a section in which the target sound source signal does not exist from among the sound source signals by multiplying the output signal by a VAD weight based on a silent section detected by the detector 650. The below example Equation 8 is obtained by reflecting this process in Equation 7 for generating an output signal.

$$\tilde{X}(w_k, n) = f\{X_R(w, n), X_L(w, n), k\} \times \alpha(w_k, n) \times \beta_{VAD}(n) \quad \text{Equation 8}$$

$$\beta_{VAD}(n) = \begin{cases} C_{speech} \\ C_{noise} \end{cases}$$

Here, $\beta_{VAD}(n)$ denotes a VAD weight, having a value in a range between 0 and 1. The VAD weight will be $C_{speech}$ close to 1 if it is determined that a target sound source exists in a current frame and will be $C_{noise}$ close to 0 if it is determined that only noise exists in the current frame.

In the noise canceling apparatus according to the current embodiment, since a VAD weight based on a silent section detected by the detector 650 is multiplied by an output signal by the noise signal canceller 640, a signal component is maintained in a section in which the target sound source exists, and interference noise existing in a silent section is more effectively cancelled.

Figure 7:
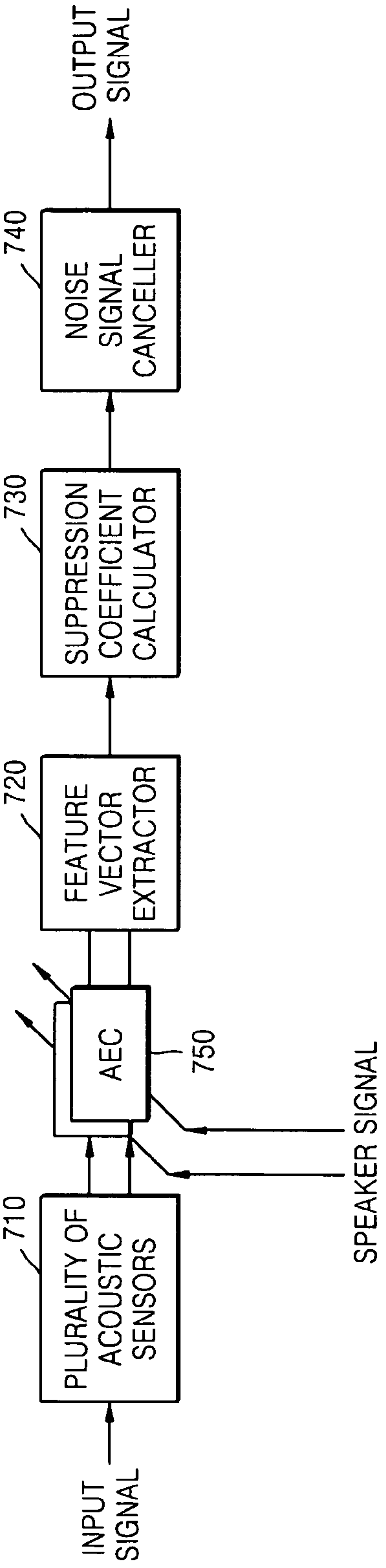
FIG. 7 is a block diagram of a noise canceling apparatus, which includes a configuration for canceling an echo, according to another embodiment of the present invention.

FIG. 7 is a block diagram of a noise canceling apparatus, which includes a configuration for canceling an echo, according to another embodiment of the present invention. Referring to FIG. 7, an acoustic echo canceller 750 is added to the block diagram illustrated in FIG. 3. Since a plurality of acoustic sensors 710, a feature vector extractor 720, a suppression coefficient calculator 730, and a noise signal canceller 740 were described with reference to the embodiment illustrated in FIG. 3, mainly only the acoustic echo canceller 750 will now be described.

The acoustic echo canceller 750 cancels an acoustic echo generated when a signal output from the noise signal canceller 740 is input through the plurality of acoustic sensors 710. In general, when a microphone is located adjacent to a speaker, sound output from the speaker is input to the microphone. That is, an acoustic echo whereby a user's voice is heard again as an output of a speaker of the user in bidirectional calling is generated. Since this echo causes great inconvenience to the user, an echo signal must be cancelled, and this is called acoustic echo cancellation (AEC). A process of achieving the AEC will now be briefly described.

It is assumed that a mixed sound containing an output sound propagated from a speaker besides a user's voice and interference noise is input to the plurality of acoustic sensors 710. A specific filter can be used as the acoustic echo canceller 750 illustrated in FIG. 7, and this filter cancels an output signal of a speaker (not shown) from a sound source signal input through the plurality of acoustic sensors 710 by receiving an output signal input to the speaker as a parameter. This filter can be configured with an adaptive filter for canceling an acoustic echo contained in a sound source signal by feeding back an output signal continuously input to the speaker over time.

For this AEC method, various algorithms, such as a least mean square (LMS) method, normalized least mean square (NLMS) method, and recursive least square (RLS) method, have been introduced, and methods of implementing the AEC using the various algorithms are well known to those of ordinary skill in the art, and thus the methods will not be described here.

Even when a microphone and a speaker are close to each other in the use of the noise canceling apparatus according to the current embodiment, unnecessary noise, such as an acoustic echo, due to an output sound propagated from the speaker can be cancelled, and simultaneously, interference noise except for a target sound can be cancelled.

Figure 8:
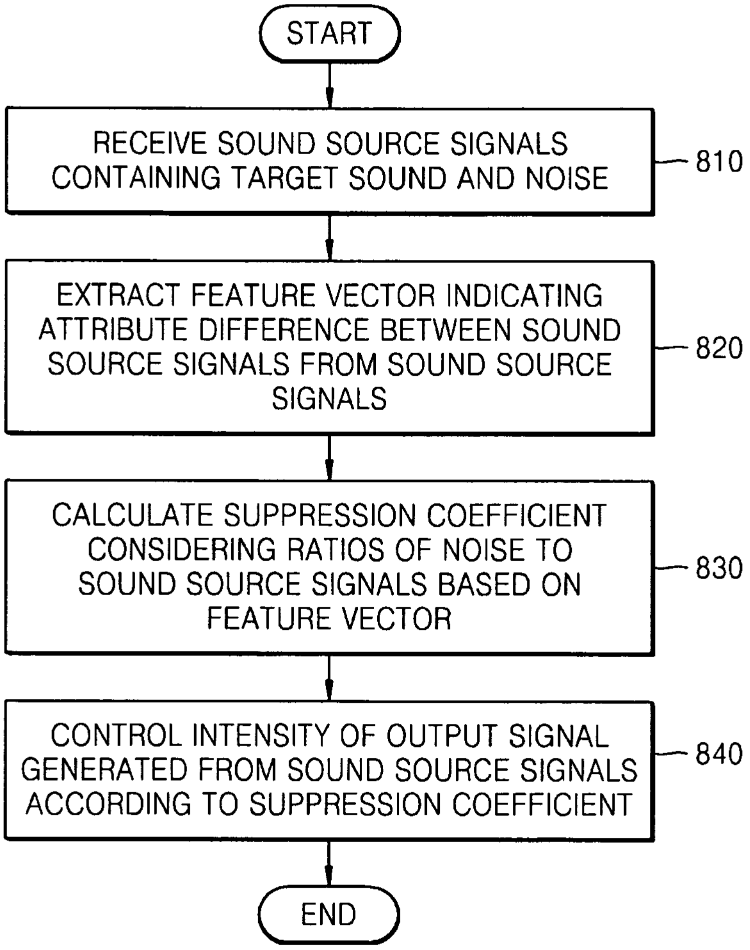
FIG. 8 is a flowchart illustrating a noise canceling method, according to an embodiment of the present invention.

FIG. 8 is a flowchart illustrating a noise canceling method, according to an embodiment of the present invention.

Referring to FIG. 8, in operation 810, sound source signals containing a target sound and interference noise are input. Since operation 810 is the same as the sound source signal input process performed by the plurality of acoustic sensors 310 illustrated in FIG. 3, a detailed description thereof will be omitted here.

In operation 820, at least one feature vector indicating an attribute difference between the sound source signals is extracted from the input sound source signals. Since operation 820 is the same as the process of extracting a feature vector, such as an amplitude ratio or a phase difference between sound source signals in the feature vector extractor 320 illustrated in FIG. 3, a detailed description thereof will be omitted here.

In operation 830, a suppression coefficient considering ratios of noise to the sound source signals is calculated based on the extracted feature vector. Since operation 830 is the same as the process of calculating a suppression coefficient for suppressing sound source signals according to ratios of noise to the sound source signals in the suppression coefficient calculator 330, a detailed description thereof will be omitted here.

In operation 840, the intensity of an output signal generated from the sound source signals is controlled according to the calculated suppression coefficient. Since operation 840 is the same as the process of canceling a noise signal contained in a sound source signal by multiplying the output signal by the suppression coefficient in the noise signal canceller 340, a detailed description thereof will be omitted here.

In addition to the above described embodiments, embodiments of the present invention can also be implemented through computer readable code/instructions in/on a medium, e.g., a computer readable medium, to control at least one processing element to implement any above described embodiment. The medium can correspond to any medium/media permitting the storing and/or transmission of the computer readable code.

The computer readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as media carrying or controlling carrier waves as well as elements of the Internet, for example. Thus, the medium may be such a defined and measurable structure carrying or controlling a signal or information, such as a device carrying a bitstream, for example, according to embodiments of the present invention. The media may also be a distributed network, so that the computer readable code is stored/transferred and executed in a distributed fashion. Still further, as only an example, the processing element could include a processor or a computer processor, and processing elements may be distributed and/or included in a single device.

As described above, the noise canceling method, according to an embodiment of the present invention, can effectively cancel interference noise by using a suppression coefficient calculated based on a feature vector due to an attribute difference between a sound source signal corresponding to a target sound and a sound source signal corresponding to noise.

While aspects of the present invention has been particularly shown and described with reference to differing embodiments thereof, it should be understood that these exemplary embodiments should be considered in a descriptive sense only and not for purposes of limitation. Descriptions of features or aspects within each embodiment should typically be considered as available for other similar features or aspects in the remaining embodiments.

Thus, although a few embodiments have been shown and described, it would be appreciated by those skilled in the art that changes may be made in these embodiments without departing from the principles and spirit of the invention, the scope of which is defined in the claims and their equivalents.

What is claimed is:

1. A noise canceling method comprising:

receiving sound source signals, each of the sound source signals including a target sound, the target sound having essentially no arrival time difference between the received sound source signals, and noise;

extracting, from the sound source signals, at least one feature vector indicating an attribute difference between the sound source signals;

calculating a suppression coefficient considering a ratio of the noise to a respective sound source signal, based on the at least one extracted feature vector; and canceling at least one sound source signal, among the received sound source signals, including the noise by controlling an intensity of an output signal generated from the sound source signals, the controlling being according to the calculated suppression coefficient.

2. The method of claim 1, wherein the at least one feature vector is at least one of an amplitude ratio and a phase difference between the sound source signals.

3. The method of claim 2, wherein, when the amplitude or phase difference between the sound source signals is the smaller, a suppression grade indicated by the suppression coefficient is a smaller value.

4. The method of claim 1, wherein the calculating of the suppression coefficient comprises:

comparing the feature vector and a predetermined threshold value; and determining the suppression coefficient by determining based on a result of the comparing whether either a target sound source signal or a noise signal contained in the sound source signals is dominant over the other.

5. The method of claim 1, wherein the canceling of the at least one sound source signal comprises:

generating an output signal from the sound source signals according to a predetermined rule; and multiplying the generated output signal by the calculated suppression coefficient.

6. The method of claim 5, wherein the predetermined rule comprises one of selecting a sound source signal, of the sound source signals, having less acoustic energy relative to other sound source signals, of the sound source signals, or calculating a mean value of the sound source signals as the output signal.

7. The method of claim 1, further comprising detecting a section of the received sound source signals in which the target sound does not exist from among the sound source signals by using a predetermined voice detection method, and the canceling of the at least one sound source signal comprises canceling a sound source signal corresponding to the section according to a result of the detecting.

8. The method of claim 1, further comprising canceling an acoustic echo generated when the output signal is input through acoustic sensors, by using a predetermined acoustic echo cancellation method.

9. A non-transitory computer readable medium comprising computer readable code to control at least one processing element operatively programmed to perform the method of claim 1.

10. A noise canceling apparatus comprising:

a plurality of acoustic sensors receiving sound source signals, each of the sound source signals including a target sound, having essentially no arrival time difference between the received sound source signals, and noise;

a feature vector extractor extracting, from the sound source signals, at least one feature vector indicating an attribute difference between the sound source signals;

a suppression coefficient calculator calculating a suppression coefficient considering a ratio of the noise to a respective sound source signal, based on the at least one extracted feature vector; and a noise signal canceller canceling at least one sound source signal, among the received sound source signals, including the noise by controlling an intensity of an output signal generated from the sound source signals, the controlling being according to the calculated suppression coefficient.

11. The apparatus of claim 10, wherein the at least one feature vector is at least one of an amplitude ratio and a phase difference between the sound source signals, and a signal of which at least one of the amplitude or phase is similar or the same from among the sound source signals is estimated as a sound source signal corresponding to the target sound.

12. The apparatus of claim 11, wherein, when the amplitude or phase difference between the sound source signals is the smaller, a suppression grade indicated by the suppression coefficient is a smaller value.

13. The apparatus of claim 10, wherein the suppression coefficient calculator comprises:

a comparator comparing the at least one feature vector and a predetermined threshold value; and a determiner determining the suppression coefficient by determining based on a result of the comparing whether either a target sound source signal or a noise signal contained in the sound source signals is dominant over the other.

14. The apparatus of claim 10, wherein the noise signal canceller comprises:

an output signal generator generating an output signal from the sound source signals according to a predetermined rule; and a multiplier multiplying the generated output signal by the calculated suppression coefficient.

15. The apparatus of claim 14, wherein the predetermined rule comprises one of selecting a sound source signal, of the sound source signals, having less acoustic energy relative to other sound source signals, of the sound source signals, or calculating a mean value of the sound source signals as the output signal.

16. The apparatus of claim 10, further comprising a detector detecting a section of the received sound source signals in which the target sound does not exist from among the sound source signals by using a predetermined voice detection method, and the noise signal canceller cancels a sound source signal corresponding to the section according to a result of the detecting.

17. The apparatus of claim 10, further comprising an acoustic echo canceller canceling an acoustic echo generated when the output signal is input through the acoustic sensors, by using a predetermined acoustic echo cancellation method.

18. The apparatus of claim 10, wherein positions of the acoustic sensors are symmetric to each other based on a target sound source, distances from the acoustic sensors to the target sound source are the same, and an object causing acoustic interference is located between the acoustic sensors.

19. The method of claim 1, further comprising determining whether the respective sound source signal is close to the target sound or the noise, based on a result of comparing the extracted at least one feature vector with a predetermined threshold value.

* * * * *